(12) United States Patent
Edmunds et al.

(10) Patent No.: US 9,028,485 B2
(45) Date of Patent: May 12, 2015

(54) SELF-EXPANDING COOLING ELECTRODE FOR RENAL NERVE ABLATION

(75) Inventors: Kevin Edmunds, Ham Lake, MN (US); Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 861 days.

(21) Appl. No.: 13/243,105

(22) Filed: Sep. 23, 2011

(65) Prior Publication Data

US 2012/0123406 A1 May 17, 2012

Related U.S. Application Data

(60) Provisional application No. 61/413,781, filed on Nov. 15, 2010, provisional application No. 61/491,730, filed on May 31, 2011.

(51) Int. Cl.
*A61B 18/18* (2006.01)
*A61B 18/14* (2006.01)
*A61B 18/00* (2006.01)

(52) U.S. Cl.
CPC ... *A61B 18/1492* (2013.01); *A61B 2018/00023* (2013.01); *A61B 2018/00029* (2013.01); *A61B 2018/00214* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/0072* (2013.01); *A61B 2018/00791* (2013.01); *A61B 2018/1435* (2013.01)

(58) Field of Classification Search
USPC .............................. 606/33, 41, 47; 604/95.05
See application file for complete search history.

(56) References Cited

U.S. PATENT DOCUMENTS

| 164,184 | A | 6/1875 | Kiddee |
| 1,167,014 | A | 1/1916 | O'Brien |
| 2,505,358 | A | 4/1950 | Gusberg et al. |
| 2,701,559 | A | 2/1955 | Cooper |
| 3,108,593 | A | 10/1963 | Glassman |

(Continued)

FOREIGN PATENT DOCUMENTS

| EP | 1053720 A1 | 11/2000 |
| EP | 1180004 A1 | 2/2002 |

(Continued)

OTHER PUBLICATIONS

Van Den Berg, "Light echoes image the human body," OLE, Oct. 2001, p. 35-37.

(Continued)

*Primary Examiner* — George Evanisko
(74) *Attorney, Agent, or Firm* — Seager, Tufte & Wickhem, LLC

(57) ABSTRACT

A metallic tube arrangement includes an electrode region configured to expand radially and contract radially in response to increasing and decreasing a temperature at the electrode region, respectively. The electrode region is configured for intravascular deployment and delivery of high frequency energy to target tissue of a target vessel of the body. The electrode region is configured to expand radially to a diameter sufficient to contact an inner wall of the target vessel in response to a decrease in electrode region temperature and to contract radially to a diameter smaller than a diameter of the target vessel in response to an increase in electrode region temperature.

18 Claims, 9 Drawing Sheets

(56) References Cited

U.S. PATENT DOCUMENTS

| | | |
|---|---|---|
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |

(56) References Cited

U.S. PATENT DOCUMENTS

| | | |
|---|---|---|
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |

(56) References Cited

U.S. PATENT DOCUMENTS

| | | | |
|---|---|---|---|
| 6,123,702 | A | 9/2000 | Swanson et al. |
| 6,123,703 | A | 9/2000 | Tu et al. |
| 6,123,718 | A | 9/2000 | Tu et al. |
| 6,129,725 | A | 10/2000 | Tu et al. |
| 6,135,997 | A | 10/2000 | Laufer et al. |
| 6,142,991 | A | 11/2000 | Schatzberger et al. |
| 6,142,993 | A | 11/2000 | Whayne et al. |
| 6,149,647 | A | 11/2000 | Tu et al. |
| 6,152,899 | A | 11/2000 | Farley et al. |
| 6,152,912 | A | 11/2000 | Jansen et al. |
| 6,156,046 | A | 12/2000 | Passafaro et al. |
| 6,158,250 | A | 12/2000 | Tibbals et al. |
| 6,159,187 | A | 12/2000 | Park et al. |
| 6,159,225 | A | 12/2000 | Makower |
| 6,161,048 | A | 12/2000 | Sluijter et al. |
| 6,162,184 | A | 12/2000 | Swanson et al. |
| 6,165,163 | A | 12/2000 | Chien et al. |
| 6,165,172 | A | 12/2000 | Farley et al. |
| 6,165,187 | A | 12/2000 | Reger et al. |
| 6,168,594 | B1 | 1/2001 | Lafontaine et al. |
| 6,171,321 | B1 | 1/2001 | Gifford, III et al. |
| 6,179,832 | B1 | 1/2001 | Jones et al. |
| 6,179,835 | B1 | 1/2001 | Panescu et al. |
| 6,179,859 | B1 | 1/2001 | Bates et al. |
| 6,183,468 | B1 | 2/2001 | Swanson et al. |
| 6,183,486 | B1 | 2/2001 | Snow et al. |
| 6,190,379 | B1 | 2/2001 | Heuser et al. |
| 6,191,862 | B1 | 2/2001 | Swanson et al. |
| 6,197,021 | B1 | 3/2001 | Panescu et al. |
| 6,200,266 | B1 | 3/2001 | Shokrollahi et al. |
| 6,203,537 | B1 | 3/2001 | Adrian |
| 6,203,561 | B1 | 3/2001 | Ramee et al. |
| 6,210,406 | B1 | 4/2001 | Webster |
| 6,211,247 | B1 | 4/2001 | Goodman |
| 6,217,576 | B1 | 4/2001 | Tu et al. |
| 6,219,577 | B1 | 4/2001 | Brown, III et al. |
| 6,228,076 | B1 | 5/2001 | Winston et al. |
| 6,228,109 | B1 | 5/2001 | Tu et al. |
| 6,231,516 | B1 | 5/2001 | Keilman et al. |
| 6,231,587 | B1 | 5/2001 | Makower |
| 6,235,044 | B1 | 5/2001 | Root et al. |
| 6,236,883 | B1 | 5/2001 | Ciaccio et al. |
| 6,237,605 | B1 | 5/2001 | Vaska et al. |
| 6,238,389 | B1 | 5/2001 | Paddock et al. |
| 6,238,392 | B1 | 5/2001 | Long |
| 6,241,666 | B1 | 6/2001 | Pomeranz et al. |
| 6,241,753 | B1 | 6/2001 | Knowlton |
| 6,245,020 | B1 | 6/2001 | Moore et al. |
| 6,245,045 | B1 | 6/2001 | Stratienko |
| 6,248,126 | B1 | 6/2001 | Lesser et al. |
| 6,251,128 | B1 | 6/2001 | Knopp et al. |
| 6,258,087 | B1 | 7/2001 | Edwards et al. |
| 6,273,886 | B1 | 8/2001 | Edwards et al. |
| 6,280,466 | B1 | 8/2001 | Kugler et al. |
| 6,283,935 | B1 | 9/2001 | Laufer et al. |
| 6,283,959 | B1 | 9/2001 | Lalonde et al. |
| 6,284,743 | B1 | 9/2001 | Parmacek et al. |
| 6,287,323 | B1 | 9/2001 | Hammerslag |
| 6,290,696 | B1 | 9/2001 | Lafontaine |
| 6,292,695 | B1 | 9/2001 | Webster, Jr. et al. |
| 6,293,942 | B1 | 9/2001 | Goble et al. |
| 6,293,943 | B1 | 9/2001 | Panescu et al. |
| 6,296,619 | B1 | 10/2001 | Brisken et al. |
| 6,298,256 | B1 | 10/2001 | Meyer |
| 6,299,379 | B1 | 10/2001 | Lewis |
| 6,299,623 | B1 | 10/2001 | Wulfman |
| 6,309,379 | B1 | 10/2001 | Willard et al. |
| 6,309,399 | B1 | 10/2001 | Barbut et al. |
| 6,311,090 | B1 | 10/2001 | Knowlton |
| 6,317,615 | B1 | 11/2001 | KenKnight et al. |
| 6,319,242 | B1 | 11/2001 | Patterson et al. |
| 6,319,251 | B1 | 11/2001 | Tu et al. |
| 6,322,559 | B1 | 11/2001 | Daulton et al. |
| 6,325,797 | B1 | 12/2001 | Stewart et al. |
| 6,325,799 | B1 | 12/2001 | Goble |
| 6,328,699 | B1 | 12/2001 | Eigler et al. |
| 6,346,074 | B1 | 2/2002 | Roth |
| 6,346,104 | B2 | 2/2002 | Daly et al. |
| 6,350,248 | B1 | 2/2002 | Knudson et al. |
| 6,350,276 | B1 | 2/2002 | Knowlton |
| 6,353,751 | B1 | 3/2002 | Swanson et al. |
| 6,355,029 | B1 | 3/2002 | Joye et al. |
| 6,357,447 | B1 | 3/2002 | Swanson et al. |
| 6,361,519 | B1 | 3/2002 | Knudson et al. |
| 6,364,840 | B1 | 4/2002 | Crowley |
| 6,371,965 | B2 | 4/2002 | Gifford, III et al. |
| 6,375,668 | B1 | 4/2002 | Gifford et al. |
| 6,377,854 | B1 | 4/2002 | Knowlton |
| 6,377,855 | B1 | 4/2002 | Knowlton |
| 6,379,352 | B1 | 4/2002 | Reynolds et al. |
| 6,379,373 | B1 | 4/2002 | Sawhney et al. |
| 6,381,497 | B1 | 4/2002 | Knowlton |
| 6,381,498 | B1 | 4/2002 | Knowlton |
| 6,383,151 | B1 | 5/2002 | Diederich et al. |
| 6,387,105 | B1 | 5/2002 | Gifford, III et al. |
| 6,387,380 | B1 | 5/2002 | Knowlton |
| 6,389,311 | B1 | 5/2002 | Whayne et al. |
| 6,389,314 | B2 | 5/2002 | Feiring |
| 6,391,024 | B1 | 5/2002 | Sun et al. |
| 6,394,096 | B1 | 5/2002 | Constantz |
| 6,394,956 | B1 | 5/2002 | Chandrasekaran et al. |
| 6,398,780 | B1 | 6/2002 | Farley et al. |
| 6,398,782 | B1 | 6/2002 | Pecor et al. |
| 6,398,792 | B1 | 6/2002 | O'Connor |
| 6,401,720 | B1 | 6/2002 | Stevens et al. |
| 6,402,719 | B1 | 6/2002 | Ponzi et al. |
| 6,405,090 | B1 | 6/2002 | Knowlton |
| 6,409,723 | B1 | 6/2002 | Edwards |
| 6,413,255 | B1 | 7/2002 | Stern |
| 6,421,559 | B1 | 7/2002 | Pearlman |
| 6,423,057 | B1 | 7/2002 | He et al. |
| 6,425,867 | B1 | 7/2002 | Vaezy et al. |
| 6,425,912 | B1 | 7/2002 | Knowlton |
| 6,427,118 | B1 | 7/2002 | Suzuki |
| 6,428,534 | B1 | 8/2002 | Joye et al. |
| 6,428,536 | B2 | 8/2002 | Panescu et al. |
| 6,430,446 | B1 | 8/2002 | Knowlton |
| 6,432,102 | B2 | 8/2002 | Joye et al. |
| 6,436,056 | B1 | 8/2002 | Wang et al. |
| 6,438,424 | B1 | 8/2002 | Knowlton |
| 6,440,125 | B1 | 8/2002 | Rentrop |
| 6,442,413 | B1 | 8/2002 | Silver |
| 6,443,965 | B1 | 9/2002 | Gifford, III et al. |
| 6,445,939 | B1 | 9/2002 | Swanson et al. |
| 6,447,505 | B2 | 9/2002 | McGovern et al. |
| 6,447,509 | B1 | 9/2002 | Bonnet et al. |
| 6,451,034 | B1 | 9/2002 | Gifford, III et al. |
| 6,451,044 | B1 | 9/2002 | Naghavi et al. |
| 6,453,202 | B1 | 9/2002 | Knowlton |
| 6,454,737 | B1 | 9/2002 | Nita et al. |
| 6,454,757 | B1 | 9/2002 | Nita et al. |
| 6,454,775 | B1 | 9/2002 | Demarais et al. |
| 6,458,098 | B1 | 10/2002 | Kanesaka |
| 6,461,378 | B1 | 10/2002 | Knowlton |
| 6,468,276 | B1 | 10/2002 | McKay |
| 6,468,297 | B1 | 10/2002 | Williams et al. |
| 6,470,216 | B1 | 10/2002 | Knowlton |
| 6,470,219 | B1 | 10/2002 | Edwards et al. |
| 6,471,696 | B1 | 10/2002 | Berube et al. |
| 6,475,213 | B1 | 11/2002 | Whayne et al. |
| 6,475,215 | B1 | 11/2002 | Tanrisever |
| 6,475,238 | B1 | 11/2002 | Fedida et al. |
| 6,477,426 | B1 | 11/2002 | Fenn et al. |
| 6,480,745 | B2 | 11/2002 | Nelson et al. |
| 6,481,704 | B1 | 11/2002 | Koster et al. |
| 6,482,202 | B1 | 11/2002 | Goble et al. |
| 6,484,052 | B1 | 11/2002 | Visuri et al. |
| 6,485,489 | B2 | 11/2002 | Teirstein et al. |
| 6,488,679 | B1 | 12/2002 | Swanson et al. |
| 6,489,307 | B1 | 12/2002 | Phillips et al. |
| 6,491,705 | B2 | 12/2002 | Gifford, III et al. |
| 6,494,891 | B1 | 12/2002 | Cornish et al. |
| 6,497,711 | B1 | 12/2002 | Plaia et al. |
| 6,500,172 | B1 | 12/2002 | Panescu et al. |

(56) References Cited

U.S. PATENT DOCUMENTS

| | | |
|---|---|---|
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |

(56) References Cited

U.S. PATENT DOCUMENTS

| | | |
|---|---|---|
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |

(56) References Cited

U.S. PATENT DOCUMENTS

| | | |
|---|---|---|
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |

(56) References Cited

U.S. PATENT DOCUMENTS

| | | |
|---|---|---|
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 8,647,297 B2 * | 2/2014 | Kronstedt et al. ......... 604/95.04 |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |

(56) References Cited

U.S. PATENT DOCUMENTS

| | | |
|---|---|---|
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0142801 A1 | 6/2006 | Demarais et al. |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0265014 A1 | 11/2006 | Demarais et al. |
| 2006/0265015 A1 | 11/2006 | Demarais et al. |
| 2006/0269555 A1 | 11/2006 | Salcedo et al. |
| 2006/0271111 A1 | 11/2006 | Demarais et al. |
| 2006/0276852 A1 | 12/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066957 A1 | 3/2007 | Demarais et al. |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0203480 A1 | 8/2007 | Mody et al. |
| 2007/0203549 A1 | 8/2007 | Demarais et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0015570 A1 | 1/2008 | Ormsby et al. |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |

(56) References Cited

U.S. PATENT DOCUMENTS

| | | |
|---|---|---|
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221939 A1 | 9/2009 | Demarais et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0057150 A1 | 3/2010 | Demarais et al. |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |

(56) References Cited

U.S. PATENT DOCUMENTS

| | | |
|---|---|---|
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | WO2006022790 | 3/2006 |
| WO | WO2006041881 | 4/2006 |
| WO | 2006105121 A2 | 10/2006 |
| WO | WO2007035537 | 3/2007 |
| WO | WO2007078997 | 7/2007 |
| WO | WO2007086965 | 8/2007 |
| WO | WO2007103879 | 9/2007 |
| WO | WO2007103881 | 9/2007 |
| WO | WO2007121309 | 10/2007 |
| WO | WO2007146834 | 12/2007 |
| WO | 2008014465 A2 | 1/2008 |
| WO | WO2008003058 | 1/2008 |
| WO | WO2008061150 | 5/2008 |
| WO | WO2008061152 | 5/2008 |
| WO | WO2008070413 | 6/2008 |
| WO | 2009121017 A1 | 10/2009 |
| WO | 2010067360 A2 | 6/2010 |
| WO | WO2010078175 | 7/2010 |
| WO | 2010102310 A2 | 9/2010 |
| WO | WO2010129661 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | WO2011091069 | 7/2011 |
| WO | 2011130534 A2 | 10/2011 |
| WO | WO2011130005 | 10/2011 |
| WO | WO2011139589 | 11/2011 |

(56) References Cited

FOREIGN PATENT DOCUMENTS

| WO | 2012019156 A1 | 2/2012 |
|---|---|---|
| WO | WO2012019156 | 2/2012 |
| WO | 2013049601 A2 | 4/2013 |

OTHER PUBLICATIONS

"IntraLuminal: Products," IntraLuminal Therapeutics, Inc., 2003, p. 1-9.

"Laser Catheter to Aid Coronary Surgery," TechTalk: MIT, Jan. 9, 1991, p. 1-4.

"Optical Coherence Tomography: LightLab Imaging Starts US Cardiology Clinical Investigations," LightLab Imaging Technology, 2002.

"Optical Coherence Tomography: LightLab Sees Bright Prospects for Cardiac Application of OCT Technology," LightLab Imaging Technology, 2001, vol. 27, No. 35.

"Products—Functional Measurement," Volcano Functional Measurement Products US, Mar. 24, 2003, p. 1-2.

Brown et al., "Radiofrequency capacitive heaters: the effect of coupling medium resistivity on power absorption along a mouse leg," Physics in Medicine and Biology, 1993, p. 1-12, vol. 38.

Carrington, "Future of CVI: It's all about plaque: Identification of vulnerable lesions, not 'rusty pipes,' could become cornerstone of preventive cardiology," Diagnostic Imaging, 2001, p. 1-8.

Chen et al., "Percutaneous pulmonary artery denervation completely abolishes experimental pulmonary arterial hypertension in vivo," EuroIntervention, 2013, p. 1-8.

Cimino, "Preventing plaque attack," Mass High Tech, 2001, p. 1-2.

Dahm et al., "Relation of Degree of Laser Debulking of In-Stent Restenosis as a Predictor of Restenosis Rate," The American Journal of Cardiology, 2002, p. 68-70, vol. 90.

De Korte et al., "Characterization of Plaque Components With Intravascular Ultrasound Elastography in Human Femoral and Coronary Arteries in Vitro," Circulation, Aug. 8, 2000, p. 617-623.

Durney et al., "Radiofrequency Radiation Dosimetry Handbook," Oct. 1986, p. 1-2, Fourth Edition.

Durney et al., "Radiofrequency Radiation Dosimetry Handbook: Contents," Oct. 1986, p. 1-5, Fourth Edition.

Fournier-Desseux et al., "Assessment of 1-lead and 2-lead electrode patterns in electrical impedance endotomography," Physiological Measurement, 2005, p. 337-349. Vo. 26, Institute of Physics Publishing.

Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.

Fram et al., "Low Pressure Radiofrequency Balloon Angioplasty: Evaluation in Porcine Peripheral Arteries," JACC, 1993, p. 1512-1521, Vol. 21, No. 6, American College of Cardiology.

Fujimori et al., "Significant Prevention of In-Stent Restenosis by Evans Blue in Patients with Acute Myocardial Infarction," American Heart Association, 2002.

Fujita et al., "Sarpogrelate, An Antagonist of 5-HT(2A) Receptor, Treatment Reduces Restenosis After Coronary Stenting," American Heart Association, 2002.

Gabriel, "Appendix A: Experimental Data," 1999, p. 1-21.

Gregory et al., "Liquid Core Light Guide for Laser Angioplasty," The Journal of Quantum Electronics, Dec. 1990, p. 2289-2296, vol. 26, No. 12.

Kaplan et al., "Healing after Arterial Dilatation with Radiofrequency Thermal and Nonthermal Balloon Angioplasty Sytems," Journal of Investigative Surgery, 1993, p. 33-52, vol. 6.

Kolata, "New Studies Question Value of Opening Arteries," The New York Times, Mar. 21, 2004, p. 1-5.

Konings et al., "Development of an Intravascular Impedance Catheter for Detection of Fatty Lesions in Arteries," IEEE Transactions on Medical Imaging, Aug. 1997, p. 439-446, vol. 16, No. 4.

Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.

Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.

Lima et al., "Efficacy and Safety of Oral Sirolimus to Treat and Prevent In-Stent Restenosis: A Pilot Study Results," American Heart Association, 2002, p. 2929.

Lima et al., "Systemic Immunosuppression Inhibits In-Stent Coronary Intimal Proliferation in Renal Transplant Patients," American Heart Association, 2002, p. 2928.

Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.

Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.

Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.

Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.

Romer et al., "Histopathology of Human Coronary Atherosclerosis by Quantifying Its Chemical Composition With Raman Spectroscopy," Circulation, 1998, p. 878-885, vol. 97.

Schauerte et al., "Catheter Ablation of Cardiac Autonomic Nerves for Prevention of Vagal Atrial Fibrillation," Circulation, 2000, p. 2774-2780, vol. 102.

Scheller et al., "Intracoronary Paclitaxel Added to Contrast Media Inhibits In-Stent Restenosis of Porcine Coronary Arteries," American Heart Association, 2002, p. 2227.

Scheller et al., "Potential solutions to the current problem: coated balloon," EuroIntervention, 2008, p. C63-C66, vol. 4 (Supplement C).

Shaffer, "Scientific basis of laser energy," Clinics in Sports Medicine, 2002, p. 585-598, vol. 21.

Shmatukha et al., "MRI temperature mapping during thermal balloon angioplasty," Physics in Medicine and Biology, 2006, p. N163-N171, vol. 51.

Slager et al., "Vaporization of Atherosclerotic Plaques by Spark Erosion," J Am Coll Cardiol, 1985, p. 21-25.

Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.

Suselbeck et al., "In vivo intravascular electric impedance spectroscopy using a new catheter with integrated microelectrodes," Basic Res Cardiol, 2005, p. 28-34, vol. 100.

Suselbeck et al., "Intravascular electric impedance spectroscopy of atherosclerotic lesions using a new impedance catheter system," Basic Res Cardiol, 2005, p. 446-452, vol. 100.

Tepe et al., "Local Delivery of Paclitaxel to Inhibit Restenosis during Angioplasty of the Leg," The New England Journal of Medicine, 2008, p. 689-699, vol. 358.

CardioVascular Technologies Inc., "Heated Balloon Device Technology," 11 pages, 2008.

Strategic Business Development, Inc., "Thermal and Disruptive Angioplasty: A Physician's Guide," 8 pages, 1990.

Zhang et al., "Non-contact Radio-Frequency Ablation for Obtaining Deeper Lesions," IEEE Transaction on Biomedical Engineering, vol. 50, No. 2, 6 pages, Feb. 2003.

Lazebnik et al., "Tissue Strain Analytics Virtual Touch Tissue Imaging and Qualification," Siemens Whitepaper, Oct. 2008, 7 pages.

Zhou et al., "Mechanism Research of Cryoanalgesia," Forefront Publishing Group, 1995.

Florete, "Cryoablative Procedure for Back Pain," Jacksonville Medicine, Oct. 1998, 10 pages.

(56) References Cited

OTHER PUBLICATIONS

Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
US 8,398,630, 3/2013, Demarais et al. (withdrawn).
Gabriel, "Appendix C: Modeling the frequency dependence of the dielectric properties to a 4 dispersions spectrum," p. 1-49, Nov. 6, 1997.
Han et al., "Third-Generation Cryosurgery for Primary and Recurrent Prostate Caner," BJU International, vol. 93, pp. 14-18, 2004.
Omura et al., "A Mild Acute Compression Induces Neurapraxia in Rat Sciatic Nerve," The International Journal of Neuroscience, vol. 114 (12), pp. 1561-1572, Dec. 2004.
"Optical Coherence Tomography: Advantages of OCT," LightLab Imaging Technology, printed Sep. 3, 2003.
"Optical Coherence Tomography: Image Gallery Cardiovascular Procedures," LightLab Imaging Technology, printed Sep. 3, 2003.
"Optical Coherence Tomography: What is OCT?," LightLab Imaging Technology, printed Sep. 3, 2003.
"Optical Coherence Tomography: Why Use OCT?," LightLab Imaging Technology, printed Sep. 3, 2003.
Popma et al., "Percutaneous Coronary and Valvular Intervention," Braunwald's Heart Disease: A Textbook of Cardiovascular Medicine, 7th edition, p. 1364-1405, 2005.

\* cited by examiner

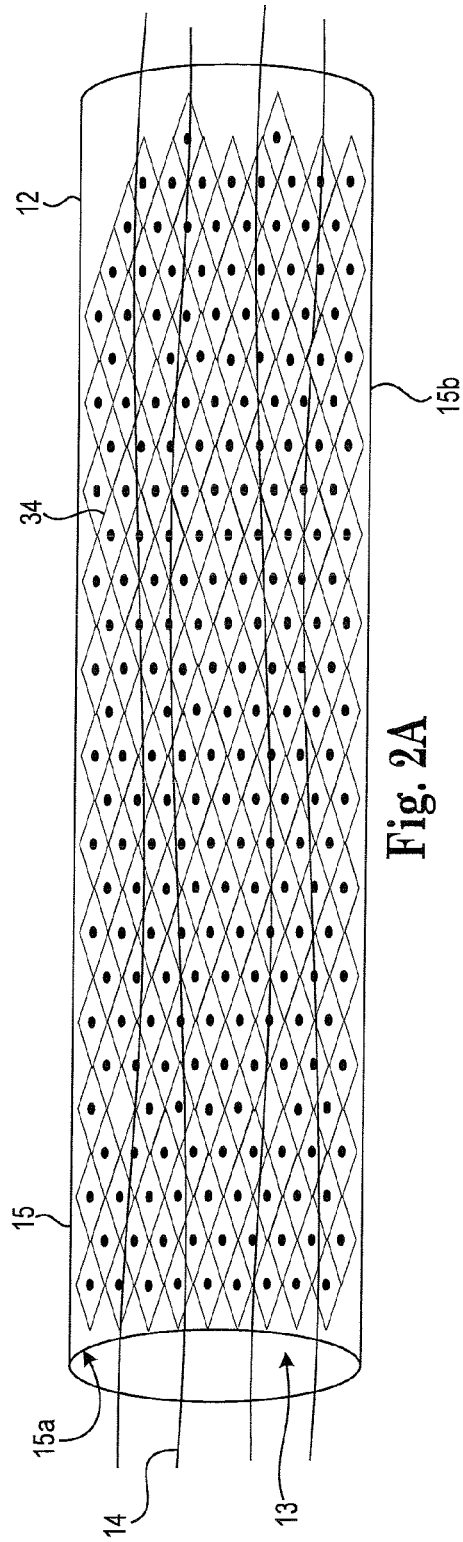
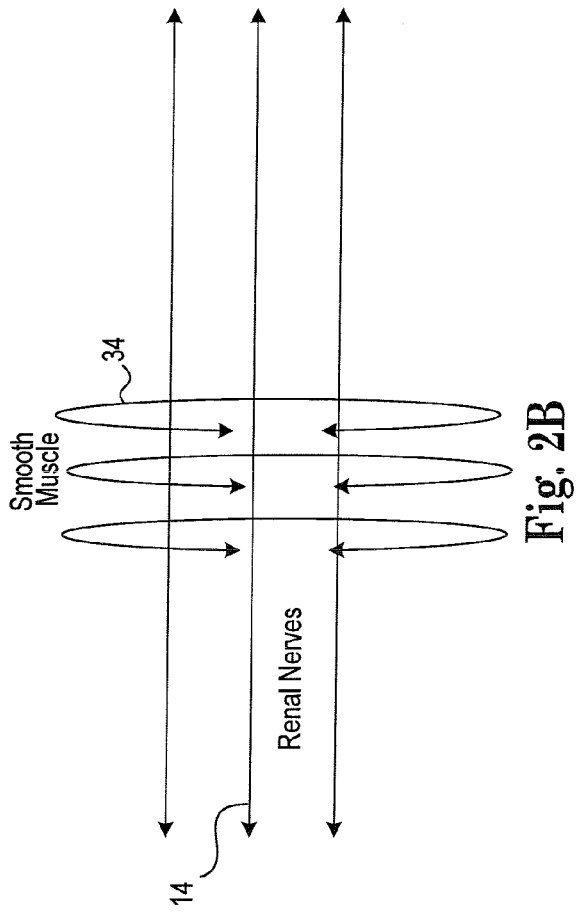
Fig. 2A
Fig. 2B

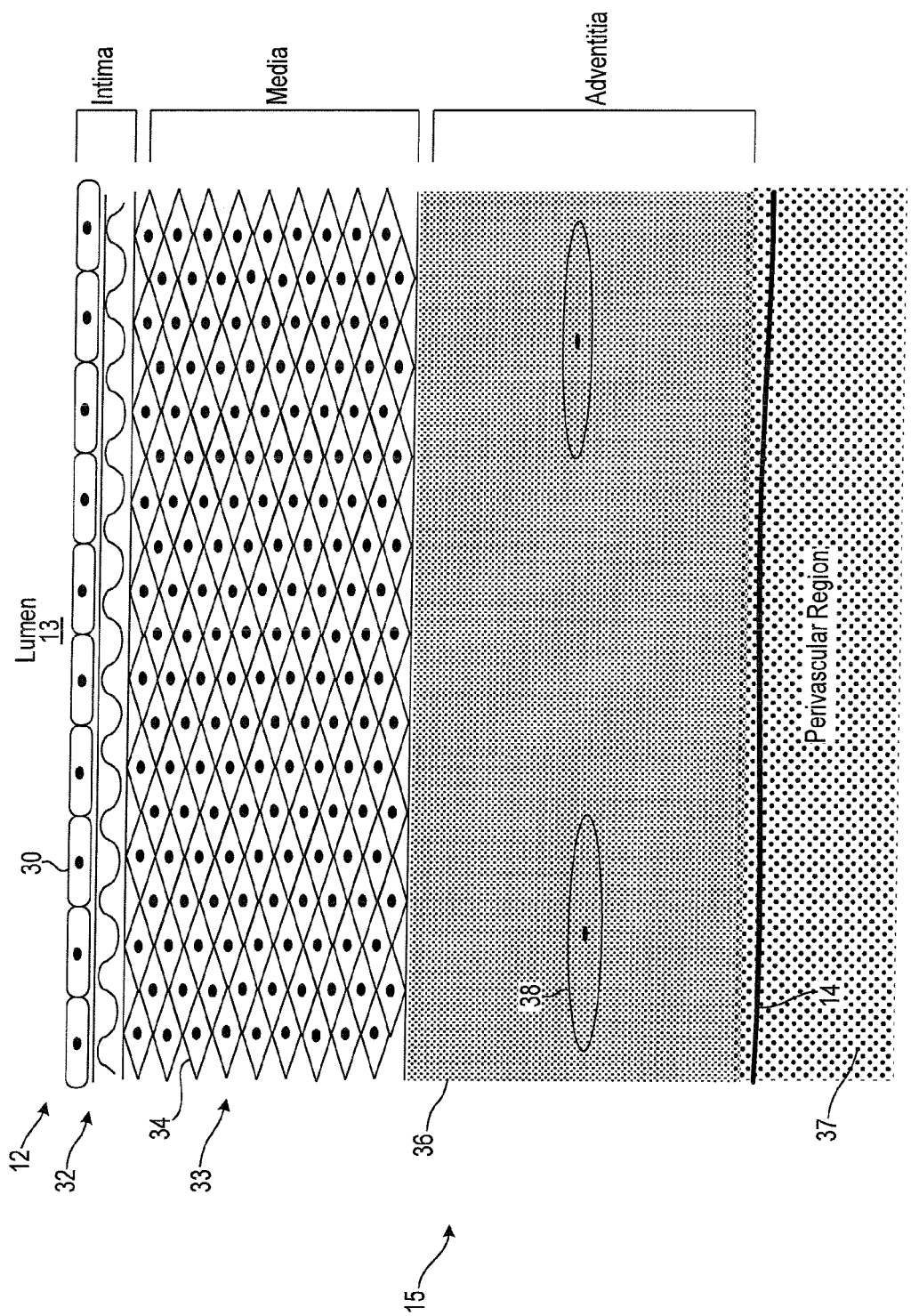

SELF-EXPANDING COOLING ELECTRODE FOR RENAL NERVE ABLATION

RELATED PATENT DOCUMENTS

This application claims the benefit of Provisional Patent Application Ser. Nos. 61/413,781 filed Nov. 15, 2010 and 61/491,730 filed May 31, 2011, to which priority is claimed pursuant to 35 U.S.C. §119(e) and which are hereby incorporated herein by reference.

SUMMARY

Embodiments of the disclosure are directed to apparatuses and methods for ablating target tissue from within a vessel or other structure of the body. Embodiments of the disclosure are directed to apparatuses and methods for ablating perivascular renal nerves from within the renal artery for the treatment of hypertension. Embodiments of the disclosure include a self-expanding cooling electrode configured to deliver high frequency energy to innervated perivascular tissue adjacent a renal artery while providing protective cooling for the renal artery. Embodiments of a self-expanding cooling electrode include various tube arrangements constructed from metallic material that expands and contracts in response to changes in temperature, and that provide for concurrent self-expansion and protective cooling in response to a reduction in electrode temperature lower than a neutral temperature, such as an ambient temperature of the human body.

In accordance with various embodiments, an apparatus includes a metallic tube arrangement comprising an electrode region configured to expand radially and contract radially in response to increasing and decreasing a temperature at the electrode region, respectively. The electrode region is configured for intravascular deployment and delivery of high frequency energy to target tissue of a target vessel of the body. The electrode region is configured to expand radially to a diameter sufficient to contact an inner wall of the target vessel in response to a decrease in electrode region temperature and to contract radially to a diameter smaller than a diameter of the target vessel in response to an increase in electrode region temperature.

According to various embodiments, an apparatus includes a metallic tube arrangement comprising a proximal end, a distal end, an inlet, and an outlet. The distal end comprises a coil section and the proximal end comprises the inlet adapted to receive thermal transfer fluid. At least the coil section of the tube arrangement is dimensioned for deployment within a target vessel. The coil section is configured to expand radially to a diameter sufficient to contact an inner wall of the target vessel in response to receiving cooled thermal transfer fluid. At least a portion of the coil section defines an electrode configured to deliver high frequency energy to target tissue. The proximal end of the metallic tube arrangement is configured to electrically couple to an electrical energy generator. The coil section is configured to contract radially to a diameter smaller than an inner wall of the target vessel in response to removal of the cooled thermal transfer fluid via the outlet.

Various embodiments are directed to methods that involve supplying thermal transfer fluid to a metallic tube arrangement positioned within a target vessel of the body. The tube arrangement comprises a coiled section having a diameter that changes in response to changing a temperature of the thermal transfer fluid. Methods further involve increasing the diameter of the coiled section such that portions of the coiled section contact portions of the target vessel in response to decreasing the temperature of the thermal transfer fluid, delivering high frequency energy to the target vessel from one or more electrode portions of the tube arrangement while the coiled section portions are in contact with the target vessel portions, and decreasing the diameter of the coiled section to a diameter less than a diameter of the target vessel in response to increasing the temperature of the thermal transfer fluid.

These and other features can be understood in view of the following detailed discussion and the accompanying drawings.

BRIEF DESCRIPTION OF THE DRAWINGS

FIGS. 2A and 2B illustrate sympathetic innervation of the renal artery;

FIG. 3A illustrates various tissue layers of the wall of the renal artery;

DETAILED DESCRIPTION

Figure 1:
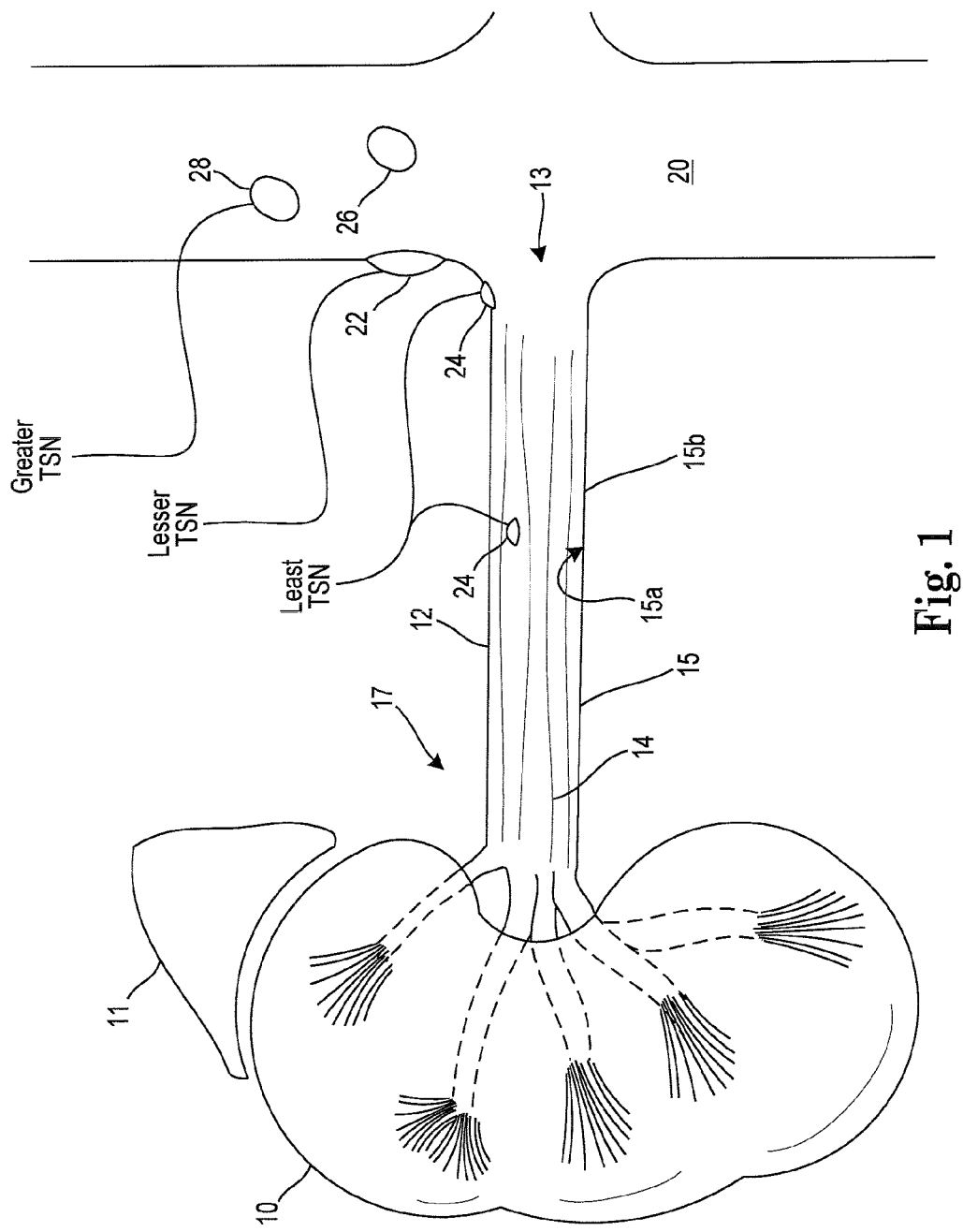
FIG. 1 is an illustration of a right kidney and renal vasculature including a renal artery branching laterally from the abdominal aorta.

Embodiments of the disclosure are directed to apparatuses and methods for improved vessel wall contact and control in ablation of target tissue, such as perivascular renal nerves for the control of hypertension. Embodiments of the disclosure are directed to various methods of ablating tissue at a short distance while protecting closer tissue. Embodiments of the disclosure are directed to methods of constructing a self-expanding tubular cooling RF electrode.

Maintaining good contact with a wall of the renal artery during ablation of perivascular renal nerves has been difficult. Conventional approaches often have problems in obtaining good contact between an intravascular ablation device and the artery wall, resulting in ineffective ablation of target nerves, or resulting in undesirable injury to arterial wall tissue. If contact is variable, the tissue temperatures are not well controlled, and an ablative temperature may not be achieved in the target tissue, while temperature in other areas, such as portions of the artery wall, may deviate enough to cause unwanted arterial tissue injury. For ideal anatomy, good vessel apposition can be achieved more easily, but especially with tortuous or diseased renal arteries, there can be very poor contact to effectively and predictably transfer heat, electrical current, or other energy from an ablation device to the target tissue.

Various embodiments are directed to ablation devices and methods that provide for improved vessel contact, as well as cooling the vessel at the line of contact, for reduced vessel injury. According to some embodiments, an ablation apparatus includes a metallic coiled structure which expands when it is cooled. The expanded coiled structure makes good contact with the vessel wall, and then portions of the coiled structure are used as RF electrodes to deliver energy to the nearby tissues. The coiled structure preferably includes a coiled metallic tube. Cooling fluid is passed through the coiled tube to concurrently cause coil expansion and to cool and protect the vessel wall.

The cooled coiled structure prevents thermal injury to the vessel where the coiled structure contacts the vessel wall, while RF energy delivered from the electrode(s) is propagated beyond the extent of the cooled region. As such, a single coiled structure can provide improved vessel contact, RF ablation of target tissue, and cooling for vessel wall protection simultaneously.

Thermal memory metal tubing, for example, can be used for the coiled structure. As the temperature is lowered or raised from a neutral temperature, the coiled structure loosens or tightens, and moves outward toward the vessel wall or inward away from the vessel wall, depending on the temperature. A cooled fluid can be passed through the coiled structure, causing the coiled structure of the electrode to expand outward toward the artery wall. The coiled structure can be adapted for phase-change cryothermal cooling by incorporating one or more orifices or narrowings to induce the phase change, or a simple cooled fluid can be used since the amount of tissue to be cooled is relatively small.

The side of the coiled structure oriented away from the artery wall can be insulated to reduce heat transfer from the blood, so that local vessel wall cooling and protection is more effective. When cooling of the coiled structure is terminated, the coiled structure deforms away from the vessel wall, to form a lower profile for introduction or removal of the device to and from the lumen of a target vessel. After delivering the device into the lumen of the target vessel, the coiled structure automatically self-deploys to achieve good vessel wall contact in response to cooling. After completion of an ablation procedure, the coiled structure of the electrode returns to a low profile configuration when the cooling is terminated.

A return tube can be included in the construction of the coiled electrode structure for handling spent cooling fluid. The return tube can be a parallel coil, or a straight tube extending through the center of the coiled structure, or other shape. A positioning sheath is preferably provided for introduction and advancement of the coiled structure within the vasculature. The self-expanding coiled structure is coupled to an external control system which provides cooling fluid and RF energy to the coiled structure.

According to various embodiments, an expandable cooling structure which incorporates a thermally activated RF electrode is constructed as an elongated tube having a length sufficient to extend between a patient's renal artery and a percutaneous access location of the patient's body. Most of the elongated tube is preferably insulated and used to conduct RF energy and cooling fluid to an expandable cooling electrode provided at the distal end of the elongated tube. Exposed portions of the coiled structure act as an RF electrode(s) to deliver energy to innervated perivascular renal tissue. The cooled coiled structure prevents thermal injury to the renal artery where the coiled structure contacts the renal artery wall, while the RF energy is delivered farther from the electrode(s) than the extent of the cooled region.

The coiled structure is preferably delivered into the lumen of the renal artery using a delivery sheath from an aortal access location. The sheath can either be retracted from the coiled structure or the coiled structure can be advanced out of the sheath's distal tip. The coiled structure can be in direct contact with the artery wall, rather than contained within a catheter balloon as in prior cryothermal approaches. This arrangement provides for improved wall contact for both cooling and RF ablation, and does not block blood flow within the renal artery. This allows the heating and cooling to be activated simultaneously and for an extended duration treatment if required. Using the various thermal shape-change structures disclosed herein, as the temperature is lowered or raised from a neutral temperature, the coiled structure loosens or tightens, and moves outward toward the artery wall or inward away from the artery wall, depending on the temperature.

Various embodiments of the disclosure are directed to apparatuses and methods for renal denervation for treating hypertension. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the disclosure. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3B:
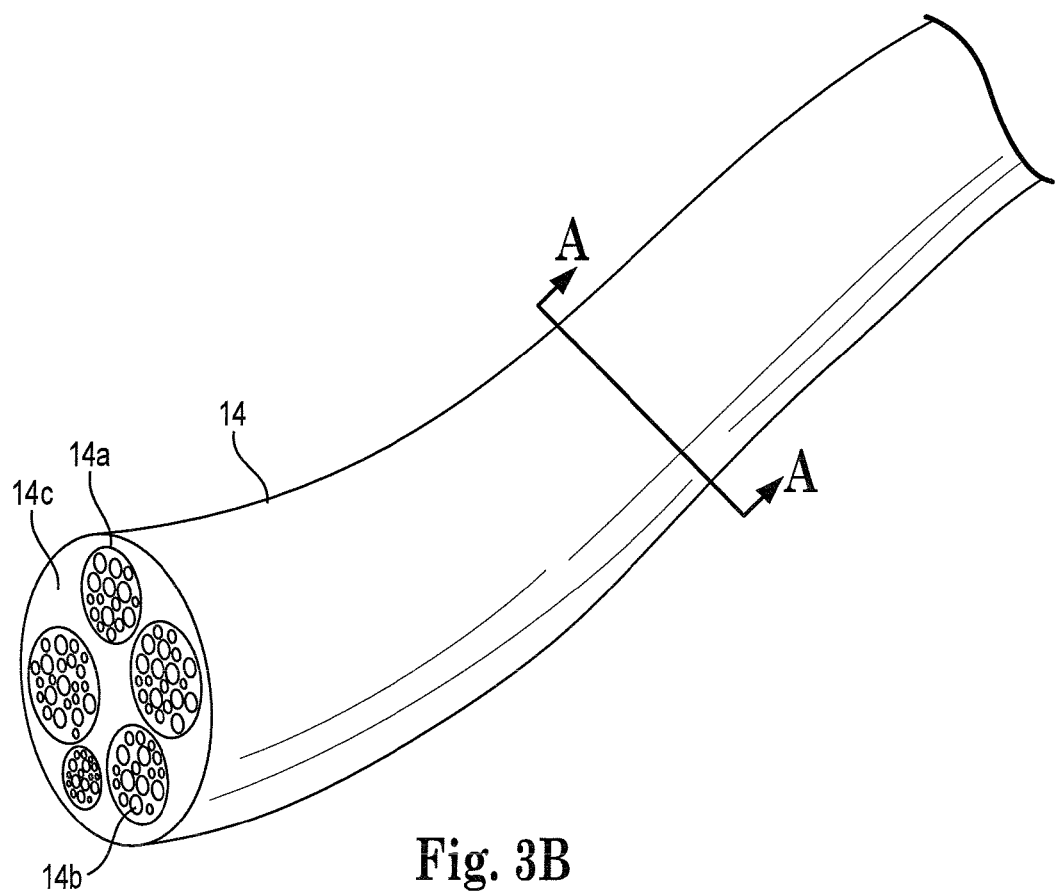
FIGS. 3B and 3C illustrate a portion of a renal nerve.

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to enervate the renal artery smooth muscle 34.

Embodiments of the disclosure may be implemented to provide varying degrees of denervation therapy to innervated renal vasculature. For example, embodiments of the disclosure may provide for control of the extent and relative permanency of renal nerve impulse transmission interruption achieved by denervation therapy delivered using a treatment apparatus of the disclosure. The extent and relative permanency of renal nerve injury may be tailored to achieve a desired reduction in sympathetic nerve activity (including a partial or complete block) and to achieve a desired degree of permanency (including temporary or irreversible injury).

Figure 3C:
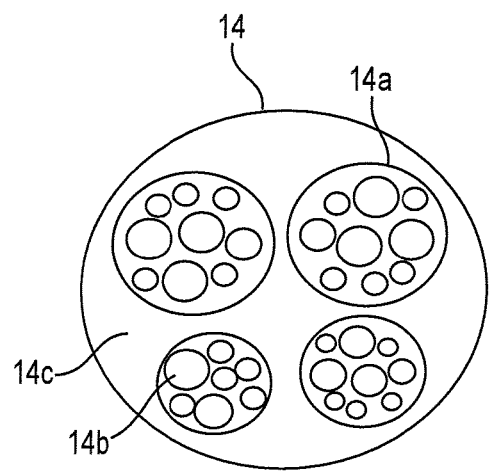

Returning to FIGS. 3B and 3C, the portion of the renal nerve 14 shown in FIGS. 3B and 3C includes bundles 14a of nerve fibers 14b each comprising axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a. In particular, the endoneurium, also referred to as the endoneurium tube or tubule, is a layer of delicate connective tissue that encloses the myelin sheath of a nerve fiber 14b within a fasciculus.

Major components of a neuron include the soma, which is the central part of the neuron that includes the nucleus, cellular extensions called dendrites, and axons, which are cable-like projections that carry nerve signals. The axon terminal contains synapses, which are specialized structures where neurotransmitter chemicals are released in order to communicate with target tissues. The axons of many neurons of the peripheral nervous system are sheathed in myelin, which is formed by a type of glial cell known as Schwann cells. The myelinating Schwann cells are wrapped around the axon, leaving the axolemma relatively uncovered at regularly spaced nodes, called nodes of Ranvier. Myelination of axons enables an especially rapid mode of electrical impulse propagation called saltation.

In some embodiments, a treatment apparatus of the disclosure may be implemented to deliver denervation therapy that causes transient and reversible injury to renal nerve fibers 14b. In other embodiments, a treatment apparatus of the disclosure may be implemented to deliver denervation therapy that causes more severe injury to renal nerve fibers 14b, which may be reversible if the therapy is terminated in a timely manner. In preferred embodiments, a treatment apparatus of the disclosure may be implemented to deliver denervation therapy that causes severe and irreversible injury to renal nerve fibers 14b, resulting in permanent cessation of renal sympathetic nerve activity. For example, a treatment apparatus may be implemented to deliver a denervation therapy that disrupts nerve fiber morphology to a degree sufficient to physically separate the endoneurium tube of the nerve fiber 14b, which can prevent regeneration and re-innervation processes.

By way of example, and in accordance with Seddon's classification as is known in the art, a treatment apparatus of the disclosure may be implemented to deliver a denervation therapy that interrupts conduction of nerve impulses along the renal nerve fibers 14b by imparting damage to the renal nerve fibers 14b consistent with neruapraxia. Neurapraxia describes nerve damage in which there is no disruption of the nerve fiber 14b or its sheath. In this case, there is an interruption in conduction of the nerve impulse down the nerve fiber, with recovery taking place within hours to months without true regeneration, as Wallerian degeneration does not occur. Wallerian degeneration refers to a process in which the part of the axon separated from the neuron's cell nucleus degenerates. This process is also known as anterograde degeneration. Neurapraxia is the mildest form of nerve injury that may be imparted to renal nerve fibers 14b by use of a treatment apparatus according to embodiments of the disclosure.

A treatment apparatus may be implemented to interrupt conduction of nerve impulses along the renal nerve fibers 14b by imparting damage to the renal nerve fibers consistent with axonotmesis. Axonotmesis involves loss of the relative continuity of the axon of a nerve fiber and its covering of myelin, but preservation of the connective tissue framework of the nerve fiber. In this case, the encapsulating support tissue 14c of the nerve fiber 14b are preserved. Because axonal continuity is lost, Wallerian degeneration occurs. Recovery from axonotmesis occurs only through regeneration of the axons, a process requiring time on the order of several weeks or months. Electrically, the nerve fiber 14b shows rapid and complete degeneration. Regeneration and re-innervation may occur as long as the endoneural tubes are intact.

A treatment apparatus may be implemented to interrupt conduction of nerve impulses along the renal nerve fibers 14b by imparting damage to the renal nerve fibers 14b consistent with neurotmesis. Neurotmesis, according to Seddon's classification, is the most serious nerve injury in the scheme. In this type of injury, both the nerve fiber 14b and the nerve sheath are disrupted. While partial recovery may occur, complete recovery is not possible. Neurotmesis involves loss of continuity of the axon and the encapsulating connective tissue 14c, resulting in a complete loss of autonomic function, in the case of renal nerve fibers 14b. If the nerve fiber 14b has been completely divided, axonal regeneration causes a neuroma to form in the proximal stump.

A more stratified classification of neurotmesis nerve damage may be found by reference to the Sunderland System as is known in the art. The Sunderland System defines five degrees of nerve damage, the first two of which correspond closely with neurapraxia and axonotmesis of Seddon's classification. The latter three Sunderland System classifications describe different levels of neurotmesis nerve damage.

The first and second degrees of nerve injury in the Sunderland system are analogous to Seddon's neurapraxia and axonotmesis, respectively. Third degree nerve injury, according to the Sunderland System, involves disruption of the endoneurium, with the epineurium and perineurium remaining intact. Recovery may range from poor to complete depending on the degree of intrafascicular fibrosis. A fourth degree nerve injury involves interruption of all neural and supporting elements, with the epineurium remaining intact. The nerve is usually enlarged. Fifth degree nerve injury involves complete transection of the nerve fiber 14b with loss of continuity.

Figure 4:
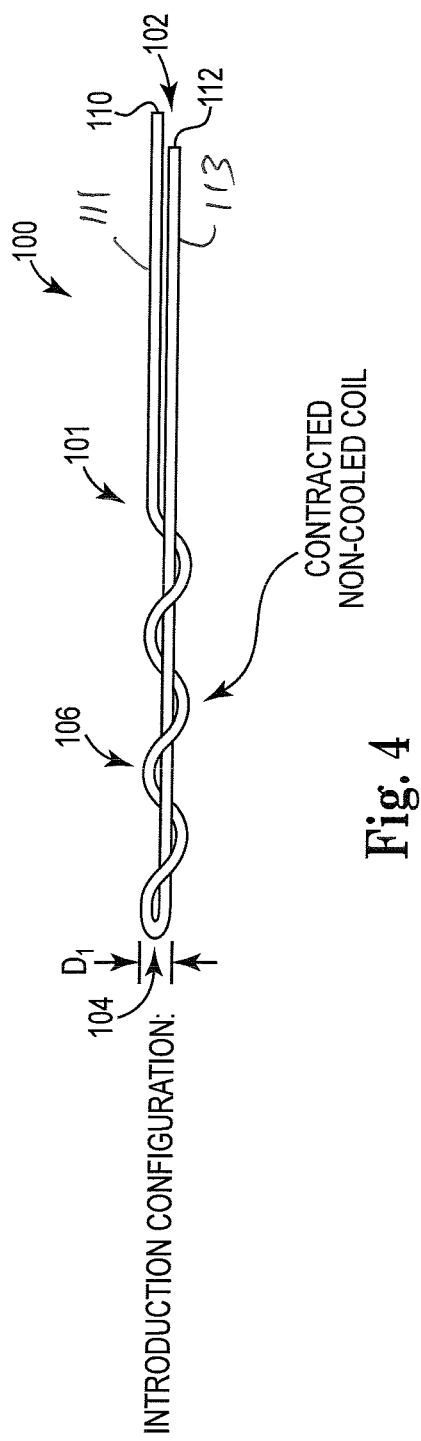
FIG. 4 shows an expandable cooling electrode adapted for renal nerve ablation in a low-profile introduction configuration in accordance with various embodiments.
Figure 5:
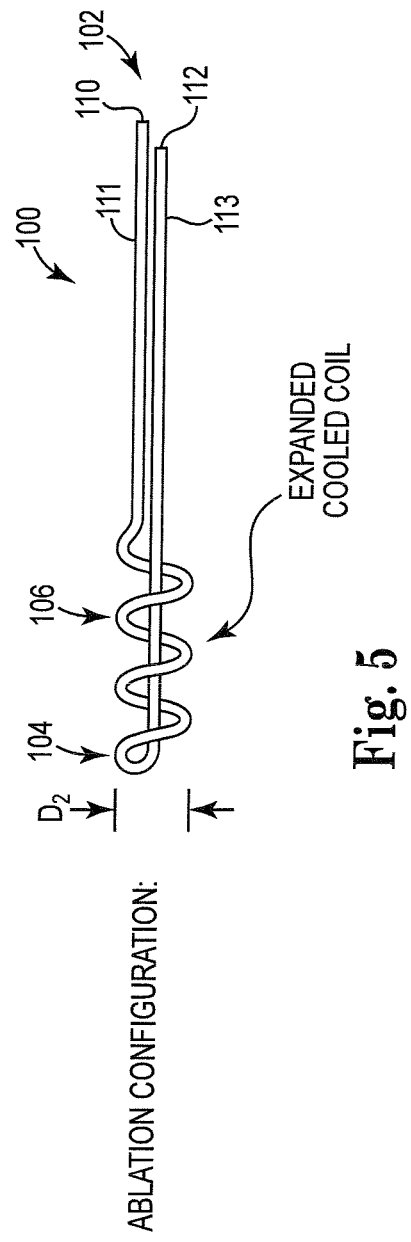
FIG. 5 shows an expandable cooling electrode adapted for renal nerve ablation in an ablation configuration in accordance with various embodiments.

Turning now to FIGS. 4 and 5, there is illustrated a self-expanding cooling electrode 100 adapted for renal nerve ablation in accordance with various embodiments. FIG. 4 shows an expandable cooling electrode 100 in a low-profile introduction configuration. When in the low-profile introduction configuration, the expandable cooling electrode 100 can be deployed within the lumen of a target vessel, such as a patient's renal artery, or other structure of the body. FIG. 5 shows the cooling electrode 100 in an expanded ablation configuration. When in the ablation configuration, the expandable cooling electrode 100 is preferably used to deliver high frequency energy (e.g., RF current) to target tissue of the vessel or other body tissue of interest.

According to various embodiments, and as shown in FIG. 4, an expandable cooling electrode 100 is constructed as a metallic tube 101 having a proximal and 102, a distal end 104, and a coil section 106 defined between the proximal and distal ends 102 and 104. The metallic tube 101 is shown having a generally elongated configuration with a portion of the metallic tube 101 wrapped around itself to form the coiled section 106. At the proximal end 102, an inlet 110 and an outlet 112 of the metallic tube 101 are aligned in a co-parallel relationship. As such, access to both the inlet 110 and the outlet 112 of the metallic tube 101 are accessible from the proximal end 102.

It is understood that the metallic tube 101 can be formed to assume a variety of configurations, and that those configurations shown in the drawings represent non-limiting examples of various embodiments. For example, the expandable cooling electrode 100 is shown in FIGS. 4 and 5 to include a supply tube 111 and a return tube 113. As illustrated, the distal end of the supply tube 111 includes the coiled section 106 wrapped around the return tube 113 which is shown to be a straight tube extending through the center of the coiled section 106. In some embodiments, the return tube 113 can be shaped to include a coiled section aligned in a co-parallel relationship with the coiled section 106 of the supply tube 111. In other embodiments, the return tube 113 need not be co-parallel with the supply tube 111 nor extend to the proximal end 102. For example, the outlet 112 can be located anywhere distal of the coiled section 106, such as at a location suited for expelling spent biocompatible thermal transfer fluid from the metallic tube 101 and into blood flowing past the metallic tube.

The supply and return tubes 111 and 113 include lumens through which a thermal transfer fluid can be transported. The materials used to fabricate the coiled section 106 of the metallic tube 101 allow the diameter of the coiled section 106 to change in response to changes in temperature. In preferred embodiments, the diameter of the coiled section 106 increases in response to cooling relative to ambient or a neutral temperature (e.g., body temperature), and decreases in response to warming relative to ambient or a neutral temperature. For example, as the temperature of the coiled section 106 is lowered or raised relative to a neutral temperature, the coiled section 106 loosens or tightens, and moves outwardly toward the vessel wall or inwardly away from the vessel wall, depending on the temperature.

According to various embodiments, the coiled section 106 of the metallic tube 101 can be formed from thermal memory metal tubing, bi-metallic tubing, bi-layer tubing, or other metallic tubing that undergoes a shape change in response to changes in temperature. Metallic materials used to form the coiled section 106 preferably have a negative thermal coefficient of expansion. More preferably, suitable metallic materials that can be used to construct the coiled section 106 includes those that have a linear negative thermal coefficient of expansion, in which the material's linear dimension changes as a function of temperature change (e.g., the fractional change in length per degree of temperature change). Portions of the metallic tube 101 proximal and distal to the coiled section 106 are preferably formed from metal or metal alloys that negligibly change shape in response to changes in temperature.

In the introduction configuration shown in FIG. 4, the coiled section 106 of the metallic tube 101 has a diameter of $D_1$. The introduction diameter, $D_1$, is preferably selected so that the expandable cooling electrode 100 can be readily and safely deployed in the lumen of a target vessel of the body, such as a renal artery. By way of example, and in the context of renal nerve ablation, the coiled section 106 may have an introduction diameter, $D_1$, of about 1 mm to about 2.5 mm. In the ablation configuration shown in FIG. 5, the coiled section 106 of the metallic tube 101 has a diameter of $D_2$. The expanded diameter, $D_2$, is preferably selected so that the coiled section 106 makes contact with an inner wall of the target vessel. In the context of renal nerve ablation, for example, the coiled section 106 may have an expanded diameter, $D_2$, of about 4 mm to about 8 mm. In various applications, the diameter of the coiled section 106 in its ablation configuration can increase between about 200% and about 800% relative to its introduction configuration.

Desired thermal response characteristics of the coiled section 106, such as the degree and/or timeliness of expansion and contraction, can be designed into the coiled section 106 depending on application particulars and the type of thermal transfer fluid used to cool the coiled section 106. A variety of thermal transfer fluids may be employed, including cold saline or cold saline and ethanol mixture, Freon or other fluorocarbon refrigerants, nitrous oxide, liquid nitrogen, and liquid carbon dioxide, for example. In some embodiments, a cooled thermal transfer fluid may be supplied by an external fluid source, circulated through the coiled section 106, and spent thermal transfer fluid returned to the external fluid source. In other embodiments, a cooled biocompatible thermal transfer fluid may be supplied by an external fluid source, circulated through the coiled section 106, and expelled into blood flowing through a target vessel, such as a renal artery.

According to some embodiments, the metallic tube 101 can be constructed to provide phase-change cryothermal cooling by incorporating one or more orifices or narrowings to induce the phase change at the coiled section 106. A liquid cryogen, for example, can be supplied to the metallic tube 101 through inlet 110. When released inside the coiled section 106, the liquid cryogen undergoes a phase change that cools the coiled section 106 by absorbing the latent heat of vaporization from the surrounding tissue, and by cooling of the vaporized gas as it enters a region of lower pressure inside the coiled section 106 (via the Joule-Thomson effect). The gas released inside the distal portion of the coiled section 106 is exhausted through outlet 112. The pressure inside the coiled section 106 may be controlled by regulating one or both of a rate at which cryogen is delivered and a rate at which the exhaust gas is extracted.

One or more temperature sensors may be provided at the coiled section 106 for measuring tube and/or arterial tissue temperature. One or more conductors can be used for coupling each of the temperature sensors to an external temperature unit.

A desired degree of shape change of the coiled section 106 can be achieved using different construction techniques and materials. The extent of shape change of the coiled section 106 can be induced over different temperature ranges, such as a relatively small temperature range or a relatively large temperature range. The change in shape of the coiled section 106 may be uniform or asymmetric depending on the construction of the coiled section 106. Other properties and characteristics can be designed into the metallic tube 101 and coiled section 106, such as flexibility, depending on the particular target vessel or other target structures of the body.

According to various embodiments, at least the coiled section 106 of the metallic tube 101 defines an electrode adapted to ablate target tissue of a target vessel, such as innervated perivascular tissue surrounding a patient's renal artery. All or a portion of the metallic tube 101, such as the coiled section 106, is preferably left exposed so that the exposed portion or portions of the metallic tube 101 define an ablation electrode, which electrically cooperates with another electrode during ablation. In some embodiments, the other electrode comprises an external pad electrode of an external generator, such as an RF generator. In such embodiments, the exposed portion(s) of the metallic tube 101 and the external electrode are operated in a monopolar configuration. According to other embodiments, the other electrode can be placed within the body in proximity to the exposed portion of the metallic tube 101. For example, the other electrode can be placed within a renal vein in proximity to the renal artery in which the expandable cooling electrode 100 is situated.

The helical shape of the expandable cooling electrode 100 allows a spiral region of perivascular renal nerve tissue to be ablated to achieve termination of renal sympathetic nerve activity in a reduced amount of time relative to conventional approaches and with minimal or no injury to the renal artery. The expandable cooling electrode 100 advantageously provides for delivery of high frequency energy for ablating perivascular renal nerve tissue and simultaneous cooling to prevent thermal damage to the renal artery wall. The thermal mechanism used to cause expansion of the coiled section 106 of the expandable cooling electrode 100 also provides protective cooling for the renal artery wall. For example, the expandable cooling electrode 100 can be deployed within the lumen of a renal artery in its introduction configuration, cooled to cause expansion of the coiled section 106 to its ablation configuration, and energized to ablate at least a 360° spiral of innervated perivascular renal tissue without having to reposition the electrode 100 during the ablation procedure and without thermally injuring the renal artery wall.

Figure 6A:
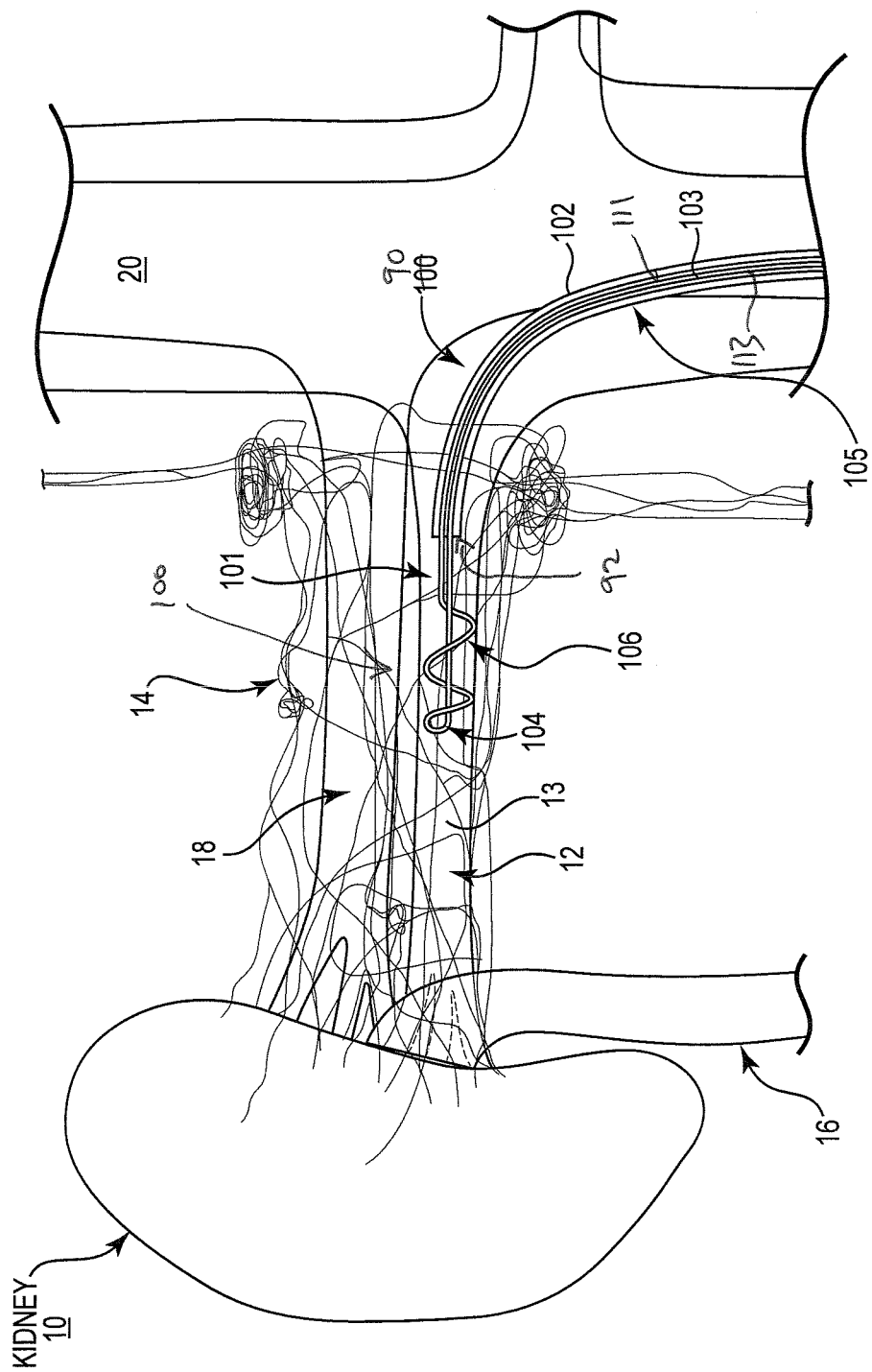
FIGS. 6A through 6C show various aspects of an ablation apparatus comprising an expandable cooling electrode extending from a distal end of a delivery sheath in accordance with various embodiments.
Figure 6C:
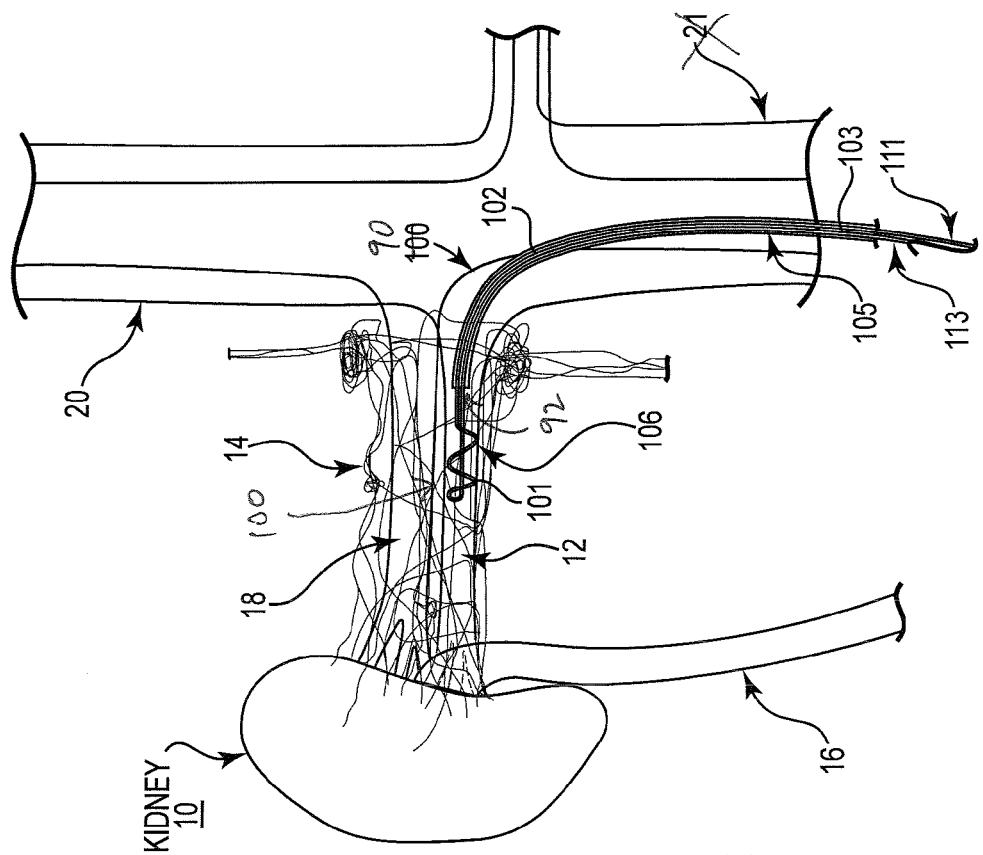
Figure 6B:
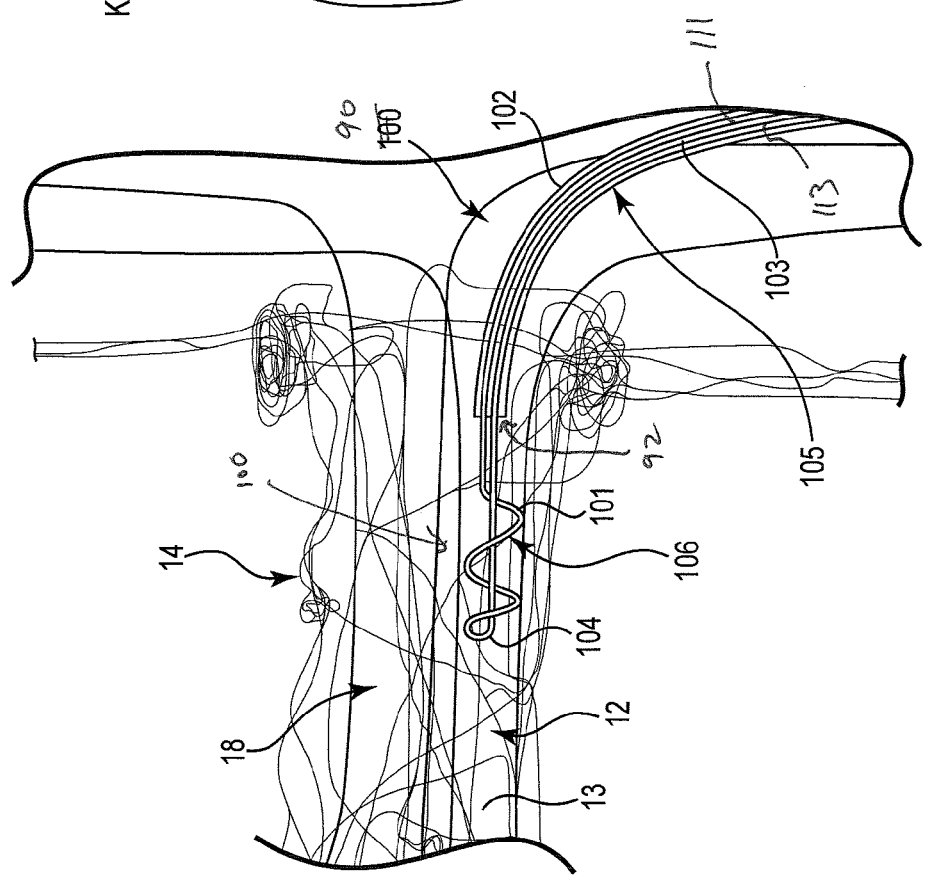

FIGS. 6A through 6C show various aspects of an ablation apparatus in accordance with various embodiments. FIGS. 6A-6C show an ablation catheter 105 comprising a sheath 90 and an expandable cooling electrode 100 extending from a distal end of the sheath 90. The sheath 90 is shown to extend into the ostium of the renal artery 12 accessed from the aorta 20 inferior to the renal artery 12. The sheath 90 includes a lumen 92 dimensioned to receive the expandable cooling electrode arrangement in its introduction configuration. The sheath 90 typically has a length sufficient to access a target vessel, such as the renal artery 12, from a perivascular access location of the patient.

The expandable cooling electrode 100 is shown coupled to a tube arrangement 103 which includes supply and return tubes 111 and 113 that respectively extend along the length of the sheath 90. The distal ends of supply and return tubes 111 and 113 are fluidly coupled to inlet 110 and outlet 112 of the metallic tube 101, respectively. The proximal ends of the supply and return tubes 111 and 113 are preferably configured to fluidly coupled to supply and return couplings of an external thermal transfer fluid source. The proximal ends of the supply and return tubes 111 and 113 are electrically coupled to an external energy source, such as an RF generator. In order to electrically insulate the proximal ends of the supply and return tubes 111 and 113 from the external thermal transfer fluid source, non-metallic fluid couplings are preferably used to fluidly coupled the proximal ends of the supply and return tubes 111 and 113 to supply and return lines of the external thermal transfer fluid source.

The supply and return tubes 111 and 113 are preferably covered with insulation to electrically and thermally isolate the two tubes 111 and 113 from each other. The inner lumen 92 of the sheath 90 may also include insulation to prevent cooled thermal transfer fluid transported through the supply tube 111 from warming due to ambient heat produced by the body. In some embodiments, a low-conductivity fluid is used to limit undesired electrical pathways.

According to other embodiments, the supply and return tubes 111 113 need not be metallic. Electrically non-conductive supply and return tubes 111 and 113 can be fluidly coupled to inlet 110 and outlet 112 of the metallic tube 101. According to such embodiments, an electrical conductor extends along the length of the sheath 102 and electrically couples the metallic tube 101 at its proximal end 102 with an external energy source. The electrical conductor can be supported on or encompassed within a lumen of the non-conductive supply tube 111 or return tube 113.

Figure 7:
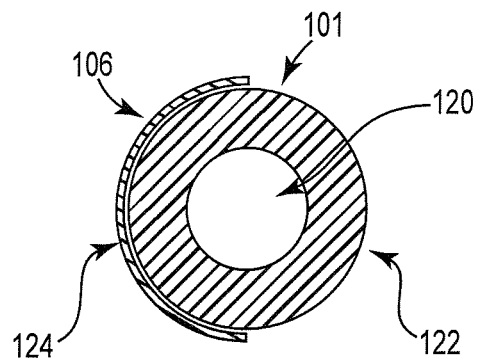
FIG. 7 shows a cross-section of a coiled section of an expandable cooling electrode having a thermal memory metallic tube construction in accordance with various embodiments.

FIG. 7 shows a cross-section of the coiled section 106 of the metallic tube 101 having a thermal memory metallic tube construction in accordance with various embodiments. In the embodiment shown in FIG. 7, the coiled section 106 is formed from a thermal memory metallic tube 122 having a lumen 123 through which thermal transfer fluid can be transported. The thermal memory metallic material used to form tube 122 of the coiled section 106 typically provides shape change over a relatively small temperature range. For example, suitable thermal memory metallic materials that provides for shape change over a relatively small temperature range include some alloys of nickel-titanium (nitinol), copper-zinc-aluminum-nickel, copper-aluminum-nickel, and some alloys of zinc, copper, gold and iron. These and other suitable thermal memory metallic materials can provide shape change over a temperature range of about 5° C., with transition chosen in the temperature range of about −10° C. to about +30° C. for this application, with about a 10° C. temperature hysteresis.

FIG. 7 further shows insulation 124 covering an outer region of the metallic tube 122 which is exposed to blood flowing in the target vessel. The insulation 124, which is an optional feature, thermally insulates the side of the coiled section 106 oriented away from the vessel wall in order to reduce heat transfer from blood, so that local vessel wall cooling and protection is enhanced.

Figure 8:
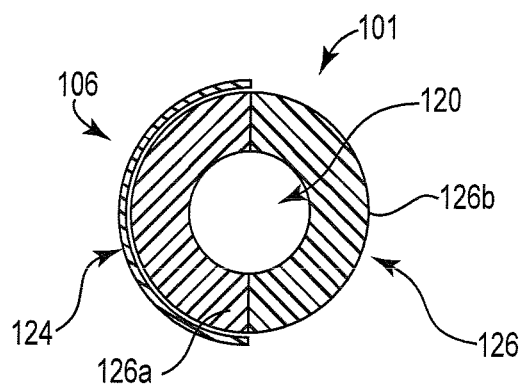
FIG. 8 shows a cross-section of a coiled section of an expandable cooling electrode having a bi-metallic tube construction in accordance with various embodiments.

FIG. 8 shows a cross-section of the coiled section 106 of the metallic tube 101 having a bi-metallic tube construction in accordance with various embodiments. The embodiment shown in FIG. 8 includes a metallic tube 101 constructed as a two-sided bi-metallic tube 101. The bi-metallic tube 126 of the coiled section 106 is preferably formed by incorporating two metals 126a and 126b having differing thermal expansion properties. According to some embodiments, a first metal 126a is used to form half of the circumference of the bi-metallic tube 101, and a second metal 126b is used to form the other half of the circumference of the bi-metallic tube 101. The first and second metals 126a and 126b have differing thermal expansion properties. The two halves are welded or otherwise bonded to one another to form the bi-metallic tube structure 126 of the coiled section 106. The bi-metallic tube 126 may include insulation 124 to thermally insulate the side of the coiled section 106 oriented away from the vessel wall for reasons previously discussed.

Use of bi-metallic tubing 126 in the construction of the coiled section 106 provides for a shape change of the coiled section 106 over a relatively large temperature range as compared to the thermal memory metallic material used to form tube 122 in the embodiment shown in FIG. 7. For example, suitable metals having differing thermal expansion properties that can be used to fabricate the bi-metallic tube 126 of the coiled section 106 include stainless steel and copper. These and other suitable bi-metallic metals can provide a gradual shape change over a several hundred degree temperature range, but the coiled section 106 can be designed to achieve the desired shape change resulting from temperature changes of about 10° C. to about 30° C. The practical temperature range is to stay above cryothermal injury temperatures, (about −10° C. or so) and below body temperature (about 37° C. or so). A smaller temperature range can be used so that the cooling required for actuating the coil is more easily achieved.

According to some embodiments, and depending on particulars of a specific application, an intravascular device of the type described above (and elsewhere) can be fabricated using metal tubing having an inner diameter that ranges between about 0.003" and 0.012", and outer diameter that ranges between about 0.006" and 0.018", and a wall thickness that ranges between about 0.0015" and 0.005".

In accordance with various embodiments, a polymer element or tube may be used in combination with a metal tube or a polymer element in the construction of the coiled section 106 (and other sections if desired). In some embodiments, the coiled section 106 is constructed using a polymer tube and a metal tube or element. In other embodiments, the coiled section 106 excludes a metal tube or element, and uses a combination of a polymeric tube and a polymer element. For example, a polymer tube may be used with an asymmetric metal or polymer element so that, due to differing thermal expansion properties, the polymer tube bends and straightens when heat is applied and removed. According to some configurations, the polymer tube can be somewhat larger in diameter and in wall thickness since the stiffness (which is usually the practical limit on size) is lower for polymers than for metal tubes.

Figure 9:
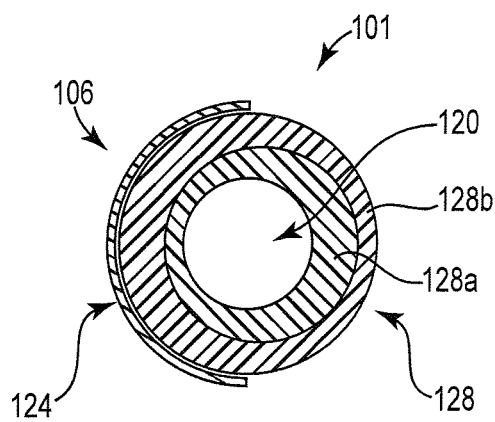
FIG. 9 shows a cross-section of a coiled section of an expandable cooling electrode having an asymmetric bi-layer tube construction in accordance with various embodiments.

FIG. 9 shows a cross-section of the coiled section 106 of the metallic tube 101 having an asymmetric bi-layer metallic tube construction in accordance with various embodiments. In the embodiment shown in FIG. 9, the coil section 106 comprises asymmetric walled tubing 128 with at least two layers of metals 128a and 128b having differing thermal expansion properties. According to some embodiments, a first tube 128a is formed from a first metal and includes a lumen 120 through which a thermal transfer fluid can be transported. The first tube 128a is formed to have an asymmetric wall thickness. A second tube 128b is formed from a second metal. The second tube 128b is formed to have an asymmetric wall thickness and a lumen dimensioned to receive the first tube 128b. The dimensions of the first and second tubes 128a and 128b, including wall thicknesses, can be selected to achieve desired expansion and shape change attributes.

A bonding material may be used to secure the first and second tubes 128a and 128b together, although frictional forces between the two tubes 128a and 128b may provide sufficient bonding. The asymmetric walled tubing 128 may include insulation 124 to thermally insulate the side of the coiled section 106 oriented away from the vessel wall for reasons previously discussed.

According to various embodiments, the thickest portion of the asymmetric walls of the first and second tubes 128a and 128b can be oriented in opposition to one another as is shown in FIG. 9. The orientation of the asymmetrical walls of the first and second tubes 128a and 128b shown in FIG. 9 maximizes the extent of shape change of the coiled section 106 in response to temperature changes. Suitable metals having differing thermal expansion properties that can be used to fabricate the asymmetric bi-layer metallic tube 128 shown in FIG. 9 include those discussed above with regard to the embodiments of FIG. 8, for example.

Figure 10:
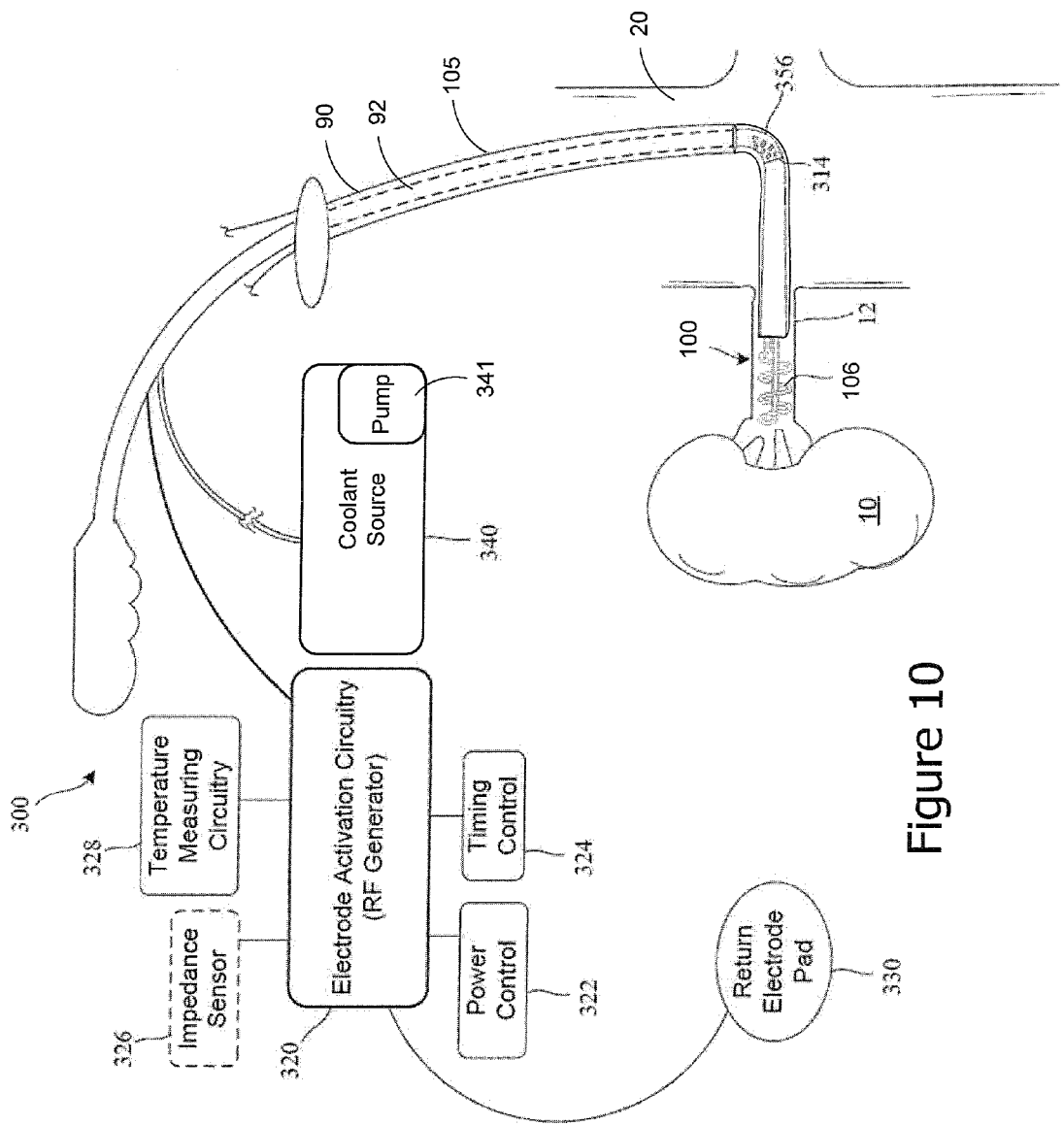
FIG. 10 shows a representative RF renal therapy apparatus in accordance with various embodiments.

FIG. 10 shows a representative RF renal therapy apparatus 300 in accordance with various embodiments of the disclosure. The apparatus 300 illustrated in FIG. 10 includes external electrode activation circuitry 320 which comprises power control circuitry 322 and timing control circuitry 324. The external electrode activation circuitry 320, which includes an RF generator, is coupled to temperature measuring circuitry 328 and may be coupled to an optional impedance sensor 326. An ablation catheter 105 of the RF renal therapy apparatus 300 includes a shaft 90 having a lumen 92 configured to receive an expandable cooling electrode 100 of a type previously described. FIG. 10 shows the coiled section 106 of the expandable cooling electrode 100 deployed within a patient's renal artery 12 in its ablation configuration.

The RF generator of the external electrode activation circuitry 320 preferably includes a pad electrode 330 that is configured to comfortably engage the patient's back or other portion of the body near the kidneys. Radiofrequency energy produced by the RF generator is coupled to the expandable cooling electrode 100 by supply and/or return tubes of the expandable cooling electrode 100 or other conductor arrangement.

Renal denervation therapy using the apparatus shown in FIG. 10 is typically performed using the expandable cooling electrode 100 and the pad electrode 330 coupled to the RF generator 320, with the RF generator 320 operating in a monopolar mode. The radiofrequency energy flows through the expandable cooling electrode 100 and perivascular space adjacent the renal artery in accordance with a predetermined activation sequence to ablate perivascular tissue which includes renal nerves.

In general, when renal artery tissue temperatures rise above about 113° F. (50° C.), protein is permanently damaged (including those of renal nerve fibers). If heated over about 65° C., collagen denatures and tissue shrinks. If heated over about 65° C. and up to 100° C., cell walls break and oil separates from water. Above about 100° C., tissue desiccates.

According to some embodiments, the electrode activation circuitry 320 is configured to control activation and deactivation of the expandable cooling electrode 100 in accordance with a predetermined energy delivery protocol and in response to signals received from temperature measuring circuitry 328. The electrode activation circuitry 320 controls radiofrequency energy delivered to the expandable cooling electrode 100 so as to maintain the current densities at a level sufficient to cause heating of the perivascular renal tissue to at least a temperature of 55° C.

Temperature sensors can be situated at the expandable cooling electrode 100 to provide continuous monitoring of renal artery tissue temperatures, and RF generator power can be automatically adjusted so that target temperatures are achieved and maintained. An impedance sensor arrangement 326 may be used to measure and monitor electrical impedance during RF denervation therapy, and the power and timing of the RF generator 320 may be moderated based on the impedance measurements or a combination of impedance and temperature measurements.

Marker bands 314 can be placed on one or multiple parts of the expandable cooling electrode 100 and/or sheath 90 to enable visualization during the procedure. A guidewire can be used to locate the renal artery to be treated, and the sheath 90 can be advanced over the guidewire and to or through the ostium of the renal artery. A hinge mechanism 356, such as a slotted tube portion of the sheath 90, can be built into the distal end of the sheath 90 to facilitate navigation of the near 90° turn from the aorta into the renal artery 12. The expandable cooling electrode 100 can then be advanced through the sheath 90 and into the renal artery.

The embodiments shown in the figures have been generally described in the context of intravascular-based ablation of perivascular renal nerves for control of hypertension. It is understood, however, that embodiments of the disclosure have applicability in other contexts, such as energy delivery and cooling from within other vessels of the body, including other arteries, veins, and vasculature (e.g., cardiac and urinary vasculature and vessels), and other tissues of the body, including various organs. For example, a self-expanding cooling electrode can be configured for deployment within the renal vein, and another electrode can be situated externally of the renal vein (e.g., within or near the target renal artery) or the patient. An appropriately sized self-expanding cooling electrode can be deployed in a cardiac chamber, such as the right atrium for treating reentrant tachyarrhythmias, or a cardiac vessel, such as the ostium of the pulmonary vein for treating atrial fibrillation. By way of further example, various embodiments may be configured for deployment in the urethra to treat benign prostatic hyperplasia (BPH) or to treat a tumor using an appropriately sized self-expanding cooling electrode of a type described hereinabove.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. An apparatus, comprising:
   a metallic tube arrangement comprising a proximal end, a distal end, an inlet, and an outlet, the distal end comprising a coil section and the proximal end comprising the inlet adapted to receive thermal transfer fluid, at least the coil section dimensioned for deployment within a target vessel;
   the coil section configured to expand radially to a diameter sufficient to contact an inner wall of the target vessel in response to receiving cooled thermal transfer fluid;
   at least a portion of the coil section defining an electrode configured to deliver high frequency energy to target tissue, the proximal end of the metallic tube arrangement configured to electrically couple to an electrical energy generator; and the coil section configured to contract radially to a diameter smaller than an inner wall of the target vessel in response to removal of the cooled thermal transfer fluid via the outlet.

2. The apparatus of claim 1, further comprising a sheath comprising a flexible shaft having a proximal end, a distal end, a length, and a lumen extending between the proximal and distal ends, the length of the shaft sufficient to access the target vessel from a percutaneous access location, and the lumen dimensioned to receive the metallic tube arrangement.

3. The apparatus of claim 1, wherein:

the coil section is configured to deliver high frequency energy to the target tissue sufficient to ablate the target tissue; and the coil section is configured to receive the cooled thermal transfer fluid at a temperature that provides protective cooling to the inner wall of the target vessel and that causes radial expansion of the coil section.

4. The apparatus of claim 1, wherein the target vessel comprises a renal artery, and the target tissue comprises perivascular tissue including renal nerves.

5. The apparatus of claim 1, further comprising:

a supply tube fluidly coupled to the inlet of the tube arrangement and having a length of the shaft sufficient to access the target vessel from the percutaneous access location; and a return tube fluidly coupled to the outlet of the tube arrangement and having a length of the shaft sufficient to access the target vessel from the percutaneous access location.

6. The apparatus of claim 1, wherein:

the thermal transfer fluid comprises a biocompatible thermal transfer fluid; and the outlet of the tube arrangement is adapted to expel spent biocompatible thermal transfer fluid into blood flowing through the target vessel.

7. The apparatus of claim 1, wherein the tube arrangement comprises a phase-change cryothermal cooling arrangement.

8. The apparatus of claim 1, wherein the coil section is formed of a single layer of a thermal memory alloy.

9. The apparatus of claim 1, wherein the coil section defines a two-sided bimetallic structure.

10. The apparatus of claim 1, wherein the coil section comprises asymmetric walled tubing with at least two layers of metals having differing thermal expansion properties.

11. The apparatus of claim 1, wherein the coil section further comprises thermal insulation covering portions of the coil section facing away from the inner wall of the target vessel.

12. The apparatus of claim 1, wherein the electrode is configured to deliver radiofrequency energy to the target tissue.

13. The apparatus of claim 1, wherein the coil section comprises one or more insulated sections and one or more exposed sections, the one or more exposed sections defining one or more electrodes.

14. An apparatus, comprising:

a metallic tube arrangement comprising an electrode region configured to expand radially and contract radially in response to increasing and decreasing a temperature at the electrode region, respectively, the electrode region configured for intravascular deployment and delivery of high frequency energy to target tissue of a target vessel of the body;

the electrode region configured to expand radially to a diameter sufficient to contact an inner wall of the target vessel in response to a decrease in electrode region temperature; and the electrode region configured to contract radially to a diameter smaller than a diameter of the target vessel in response to an increase in electrode region temperature.

15. The apparatus of claim 14, further comprising a sheath comprising a flexible shaft having a proximal end, a distal end, a length, and a lumen extending between the proximal and distal ends, the length of the shaft sufficient to access the target vessel from a percutaneous access location, and the lumen dimensioned to receive the metallic tube arrangement.

16. The apparatus of claim 14, wherein:

the electrode region further comprises a fluid channel;

the electrode region configured to expand radially to the diameter sufficient to contact the inner wall of the target vessel in response to communicating cooled thermal transfer fluid through the fluid channel; and the electrode region configured to contract radially to the diameter smaller than the target vessel diameter in response to terminating communication of cooled thermal transfer fluid through the fluid channel.

17. The apparatus of claim 14, wherein:

the electrode region is configured to deliver high frequency energy to the target tissue sufficient to ablate the target tissue; and the electrode region is configured to provide protective cooling to the inner wall of the target vessel.

18. The apparatus of claim 14, wherein the target vessel comprises a renal artery, and the target tissue comprises perivascular tissue including renal nerves.

* * * * *